United States Patent
Shodai et al.

(10) Patent No.: US 7,763,276 B1
(45) Date of Patent: Jul. 27, 2010

(54) CHEWABLE SOFT CAPSULES HAVING IMPROVED ADMINISTRATION PROPERTIES AND PROCESS FOR PRODUCING THE SAME

(75) Inventors: Hidekazu Shodai, Takatsuki (JP); Noboru Nagafuji, Sakai (JP); Toshitada Toyoda, Kobe (JP); Yuka Okada, Takatsuki (JP)

(73) Assignee: Shionogi & Co., Ltd. (JP)

( * ) Notice: Subject to any disclaimer, the term of this patent is extended or adjusted under 35 U.S.C. 154(b) by 0 days.

(21) Appl. No.: 09/914,340

(22) PCT Filed: Feb. 23, 2000

(86) PCT No.: PCT/JP00/01049

§ 371 (c)(1),
(2), (4) Date: Feb. 19, 2002

(87) PCT Pub. No.: WO00/51570

PCT Pub. Date: Sep. 8, 2000

(30) Foreign Application Priority Data

Feb. 26, 1999 (JP) .................. 11/051411

(51) Int. Cl.
*A61K 9/48* (2006.01)
*A61K 9/64* (2006.01)

(52) U.S. Cl. .................. 424/456; 424/451
(58) Field of Classification Search .................. 424/451
See application file for complete search history.

(56) References Cited

U.S. PATENT DOCUMENTS

| | | | | |
|---|---|---|---|---|
| 2,206,113 | A * | 7/1940 | Nitardy | 514/167 |
| 3,620,759 | A * | 11/1971 | Maddox | 426/78 |
| 4,219,439 | A * | 8/1980 | Miyake et al. | 264/4.4 |
| 4,342,787 | A * | 8/1982 | Rebaudieres et al. | 426/103 |
| 4,463,024 | A * | 7/1984 | Nishizawa et al. | 426/533 |
| 4,532,126 | A * | 7/1985 | Ebert et al. | 427/2.18 |
| 4,634,598 | A * | 1/1987 | Liu et al. | 426/650 |
| 4,724,136 | A * | 2/1988 | Scheibl | 424/50 |
| 4,780,316 | A * | 10/1988 | Brox | 424/456 |
| 4,800,083 | A | 1/1989 | Horn et al. | |
| 4,921,843 | A * | 5/1990 | Pasquale | 514/170 |
| 4,935,243 | A * | 6/1990 | Borkan et al. | 424/441 |
| 5,084,278 | A * | 1/1992 | Mehta | 424/441 |
| 5,563,144 | A * | 10/1996 | Damour et al. | 514/252.16 |
| 5,578,336 | A * | 11/1996 | Monte | 426/72 |
| 5,635,200 | A | 6/1997 | Douglas et al. | |
| 5,639,724 | A * | 6/1997 | Cavanak | 514/11 |
| 5,688,312 | A * | 11/1997 | Sacripante et al. | 106/31.49 |
| 5,756,543 | A * | 5/1998 | Katsuragi et al. | 514/547 |
| 5,849,787 | A | 12/1998 | Fujiwara et al. | |
| 5,859,048 | A * | 1/1999 | Oohashi et al. | 514/428 |
| 5,955,098 | A * | 9/1999 | Dugger, III | 424/435 |
| 6,027,746 | A * | 2/2000 | Lech | 424/455 |
| 6,071,523 | A * | 6/2000 | Mehta et al. | 424/400 |
| 6,297,273 | B1 * | 10/2001 | Romanczyk, Jr. | 514/456 |
| 2004/0002517 | A1 * | 1/2004 | Weisman et al. | 514/319 |
| 2004/0142031 | A1 * | 7/2004 | Haan et al. | 424/465 |

FOREIGN PATENT DOCUMENTS

| | | |
|---|---|---|
| CN | 1136446 | 11/1996 |
| CN | 1172677 A | 6/1997 |
| EP | 0544189 A1 * | 6/1993 |
| EP | 815854 | 1/1998 |
| EP | 815855 | 1/1998 |
| EP | 815864 | 1/1998 |
| EP | 0904064 B1 * | 3/1999 |
| EP | 0904064 B1 * | 10/2001 |
| GB | 2151201 A1 * | 7/1985 |
| JP | 60-058038 | 4/1985 |
| JP | 60-139617 | 7/1985 |
| JP | 61-036217 | 2/1986 |
| JP | 63-246333 | 10/1988 |
| JP | 02-212417 | 8/1990 |
| JP | 05-238954 | 9/1993 |
| JP | 7242536 A * | 9/1995 |
| JP | 10-273436 | 10/1998 |
| KR | 8802035 | 10/1988 |
| WO | WO 95/00123 | 1/1995 |
| WO | 97/38663 A2 | 10/1997 |

OTHER PUBLICATIONS

U.S. Patent No. 5,919,481 to Cody, et al. is being submitted as an English version of the Chinese patent noted above since no English translation is available.

* cited by examiner

*Primary Examiner*—S. Tran
(74) *Attorney, Agent, or Firm*—Richard M. Klein; Fay Sharpe LLP

(57) ABSTRACT

A soft capsule in which a shell is filled with fill material, and the fill material is in a solid or semi-solid form at room temperature. The soft capsule may be a chewable capsule, and the fill material may comprise a low melting point additive. The content of the low melting point additive may be 10% or more with respect to the total weight of the fill material, and may have a melting point of about 20 to 50° C. The low melting point additive may be selected from the group consisting of chocolate base, lard, coconut oil and macrogol (polyethylene glycol) as well as a combination thereof.

29 Claims, 4 Drawing Sheets

CHEWABLE SOFT CAPSULES HAVING IMPROVED ADMINISTRATION PROPERTIES AND PROCESS FOR PRODUCING THE SAME

TECHNICAL FIELD

The present invention relates to a chewable soft capsule and a method for producing the same. More particularly, the present invention relates to a soft capsule whose fill material is in a solid or semi-solid form at room temperature, and a method for producing the same.

BACKGROUND ART

Recently, there has been increasing demand for chewable capsules which can be easily ingested without water from a viewpoint of improving ingestion properties and portability of pharmaceuticals. Chewable capsules capable of being easily ingested without water are useful especially as immediate-soluble preparations for children and the elderly.

One of the dosage forms which can be used as a chewable preparation is a soft capsule. As a method for softening the shell of a soft capsule to be made suitable for chewing, a method for increasing the mix proportion of a plasticizer, such as concentrated glycerin, glycerin, or D-sorbitol, in the composition of the shell is conventionally known (e.g., see Japanese Laid-Open Publication No. 10-273436 and WO87/01034). However, as the conventional fill material of a soft capsule, an oil solution or suspension, an aqueous or alcoholic solution, or the like have been used. These fill materials are heterogeneous to the shell of a soft capsule. Therefore, when chewing, such a capsule is likely to leave an unpleasant sensation from the shell and the oiliness of an oil base in a fill material. Drugs often exhibit an unpleasant taste, such as peculiar bitterness. Since the drug-containing fill material of conventional chewable soft capsules is in a solution or suspension form, the fill material immediately spreads out in the mouth and the bitterness of the drug is sensed simultaneously with the ingestion of the capsules. This leads to a reduction in the sensation of ingestion of soft capsules.

In the case of tablets, in order to improve the sensation of ingestion, there has been reported a method for producing a tablet using granules comprising oils and fats so as to be immediately disintegrated in the mouth (see Japanese Laid-Open Publication No. 8-333243). However, there is no known soft capsule which has been known to be improved in the sensation of ingestion from the above-described viewpoint.

In the field of foods, recently, as there has been a growing interest in health, there are increasing needs for chewable capsules via which nutrients can be easily supplied. Therefore, soft capsules having an excellent sensation of ingestion are useful for applications as foods and so on, in addition to medications.

As described above, conventional chewable soft capsules are not necessarily satisfactory in terms of the sensation of ingestion due to an unpleasant sensation from the shell and the bitterness of the drugs. The present invention is intended to solve the above-described problems.

DISCLOSURE OF THE INVENTION

As a result of vigorous study by the inventors, it was found that when a soft capsule is formulated in such a manner that the fill material is in a solid or semi-solid form at room temperature, the shell and the fill material homogenized with each other when the capsule is chewed, so that an unpleasant sensation from the shell is alleviated. Particularly, the fill material of the soft capsule is preferably a low melting point additive. Specifically, when a chocolate base, such as cacao powder, bitter chocolate, or cacao butter, is formulated at an appropriate mix portion, a chewable formulation which can be easily chewed in the mouth without water can be obtained. The present invention is completed based on these findings.

According to the present invention, a soft capsule comprising fill material filling a shell is provided. The fill material is in a solid or semi-solid form at room temperature.

In one embodiment of this invention, the soft capsule is a chewable capsule.

In one embodiment of this invention, the fill material comprises a low melting point additive. The content of the low melting point additive is 10% or more, preferably 30% or more, and more preferably 50% or more with respect to the total weight of the fill material. Further, the melting point of the low melting point additive is about 20 to 50° C.

The above-described low melting point additive may be selected from the group consisting of chocolate base, lard, coconut oil and macrogol (polyethylene glycol) as well as a combination thereof. Particularly, the low melting point additive is preferably a chocolate base which may be selected from the group consisting of cacao powder, bitter chocolate and cacao butter as well as a combination thereof. Preferably, the cacao butter may include a major amount of V-type crystal and a minor amount of VI-type crystal.

In one embodiment of this invention, the fill material further comprises a sweetening agent. The sweetening agent may be selected from the group consisting of aspartame, disodium glycyrrhizinate, saccharin sodium, stevia and thaumatin as well as a combination thereof.

In one embodiment of this invention, in the soft capsule of the invention, the fill material comprises cacao butter as chocolate base, which is a low melting point additive, and aspartame as a sweetening agent.

In one embodiment of this invention, in the soft capsule of the invention, the fill material further comprise a saccharide in addition to the sweetening agent. The saccharide may be selected from the group consisting of sucrose, D-mannitol, xylitol, erythritol, D-sorbitol, maltose, reduced maltose syrup and maltitol as well as a combination thereof.

In one embodiment of this invention, in the soft capsule of the invention, the fill material further comprise an aromatic in addition to the sweetening agent. The aromatic may be chocolate flavor.

In one embodiment of this invention, in the soft capsule of the invention, the shell comprises the following components (A) and (B): (A) gelatin; and (B) one or more plasiticizers selected from (b1) to (b3), in which a total of 100 to 600 weight parts of the plasticizers is present in the shell with respect to 100 weight parts of gelatin: (b1) glycerin, (b2) saccharide plasticizer selected from the group consisting of sucrose, fructose, D-mannitol, xylitol, erythritol, D-sorbitol, maltose, reduced maltose syrup, maltitol, sucrose alcohol and isomerized sugar as well as a combination thereof, and (b3) glycol selected from the group consisting of propylene glycol and polyethylene glycol as well as a combination thereof. The plasticizers (B) may include the glycerin (b1). The shell may further comprise (C) water-insoluble cellulose in addition to (A) and (B), in which 5 to 100 weight parts of water-insoluble cellulose is present in the shell with respect to 100 weight parts of the gelatin.

In one embodiment of this invention, in the soft capsule of the invention, the shell further comprise (D) a sweetener in addition to (A) and (B). The sweetener (D) may be selected from the group consisting of saccharin sodium, stevia and thaumatin as well as a combination thereof.

In one embodiment of this invention, in the soft capsule of the invention, the fill material comprises a drug. The content of the drug may be 60% or less with respect to the total weight of the fill material.

In one embodiment of this invention, in the soft capsule of the invention, the drug is selected from the group consisting of an antipyretic analgesic drug component, a rhinitis drug component, an antitussive expectorant drug component and a vitamin component as well as a combination thereof.

In one embodiment of this invention, in the soft capsule of the invention, the fill material comprises a food.

Further, according to the present invention, a method for producing any of the above-described soft capsules comprising the step of filling the shell with the fill material is provided.

In one embodiment of this invention, in the method, the fill material comprises cacao butter as chocolate base, which is a low melting point additive, and the method further comprises the step of subjecting the fill material filling in the shell to aging at a temperature of 30 to 40° C. The aging could be conducted for 10 hours or more.

BEST MODE FOR CARRYING OUT THE INVENTION

Hereinafter, the present invention will be described in more detail.

A soft capsule of the present invention is characterized by comprising a shell into which a fill material comprising a drug or a food is filled, and in that the fill material is in a solid or semi-solid form at room temperature. "Room temperature" refers to about 1 to 30° C. "In a solid or semi-solid form" refers to that a fill material substantially does not exhibit a flow property at room temperature. A fill material may be in a powder form, and more preferably in an integrated solid or semi-solid form.

According to the present invention, since a fill material of a soft capsule is in a solid or semi-solid form, the fill material and a shell homogenize with each other in the mouth when chewing the capsule. Therefore, the unpleasant sensation typical of shells can be alleviated and the oiliness of the oil base is not sensed, thereby significantly improving the sensation of ingestion.

The soft capsule of the present invention comprising a fill material in a solid or semi-solid form at room temperature is novel. Although embodiments of use thereof are not specifically limited, a preferable embodiment thereof is a chewable capsule.

In the soft capsule of the present invention, the fill material may comprise a low melting point additive. The addition of an appropriate amount of the low melting point additive allows the entire fill material to be melted without undue heating. Therefore, the soft capsule can be easily produced without degeneration or decomposition of fill material components, such as a drug and a food, and without the occurrence of adhesion failure of the capsule.

The proportion of the low melting point additive is not particularly limited, and may be typically 10% or more, preferably 20% or more, more preferably 30% or more, even more preferably 40% or more, further preferably 50% or more, and even further 60% or more with respect to the total weight of fill material. The low melting point additive is preferably an additive capable of adjusting the dissolving temperature of the entire base for the fill material comprising the additive to higher than room temperature, and typically about 70° C. or less, preferably about 60° C. or less, more preferably about 50° C. or less, and even more preferably about 45° C. or less. "Base" refers to a fill material other than a drug in the case of a soft capsule comprising the drug, and a component of a fill material other than a food in the case of a soft capsule comprising the food.

The low melting point additive may be any additive which is pharmaceutically acceptable or appropriate for foods as long as the above-described objectives can be achieved. The melting point of such a low melting point additive may be typically in the range of about 20 to 50° C., preferably about 25 to 45° C., and more preferably about 30 to 40° C.

Preferable examples of the low melting point additive include chocolate base, lard, coconut oil and macrogol (polyethylene glycol) as well as any combination thereof. Particularly, when macrogol is used, the solubility and release properties of a slightly-soluble drug can be improved, and the absorbability of a slightly-absorbable drug can be improved. These additives are commercially available, or can be readily produced using a known preparation method. Examples of commercially available macrogol which may be preferably used in the present invention include macrogol 600, macrogol 1000, macrogol 1500, and macrogol 1540.

The chocolate base refers to known materials which can be raw materials for chocolate as well as a combination thereof. Typical chocolate bases include cacao powder, bitter chocolate, and cacao butter as well as a combination thereof. Cacao powder, bitter chocolate and cacao butter are all known as pharmaceutical additives.

By including a chocolate base in a fill material as needed, a chocolate-flavor preparation can be provided which keeps appearance as a capsule and which can be easily chewed in the mouth without water. Further, unpleasant tastes due to the drug or food will be masked.

Also, in the soft capsule of the present invention, the fill material may comprise any sweetening component which is pharmaceutically acceptable or appropriate as a food (herein referred to as a "sweetening agent"). Preferable examples of the sweetening agent include aspartame, disodium glycyrrhizinate, saccharin sodium, stevia and thaumatin as well as any combination thereof. For the sake of convenience, saccharides (described later) which may be contained in the fill material are excluded from the definition of sweetening agents.

By including a sweetening agent in a fill material as needed, it is possible to provide a preparation further suppressing unpleasant tastes, such as the bitterness of a drug or food.

The inventors have found that when cacao butter as a chocolate base is combined with aspartame as a sweetening agent, an aspartame stabilizing effect is obtained. Therefore, a soft capsule comprising a fill material comprising cacao butter as a chocolate base and aspartame as a sweetening agent is a preferred embodiment of the invention. The above-described stabilizing effect may be significant, especially when formulated in a mix proportion of cacao butter which is typically about 5% or more, and preferably about 10% to 50% with respect to the total weight of the fill material, or typically about 3 to 15 weight parts, and preferably about 3 to 12 weight parts with respect to one weight part of aspartame.

Also, in the soft capsule of the present invention, the fill material may comprise any saccharide, which is pharmaceutically acceptable or appropriate as a food, in addition to a sweetening agent. Preferable examples of a saccharide include sucrose, D-mannitol, xylitol, erythritol, D-sorbitol, maltose, reduced maltose syrup and maltitol as well as any combination thereof. Sugar alcohols are generally stable toward drugs and foods and therefore are especially preferable examples of a saccharide. For the sake of convenience, glycosides exhibiting sweetness, such as stevia described above, are excluded from the definition of saccharides.

Also, in the soft capsule of the present invention, the fill material may comprise any aromatic, which is pharmaceutically acceptable or appropriate as a food, in addition to a sweetening agent. Preferable examples of an aromatic include chocolate flavor, peppermint flavor and vanilla flavor as well as any combination thereof.

By including a saccharide and/or an aromatic in addition to a sweetening agent into a fill material as needed, it is possible to provide a soft capsule having a further improved sensation of ingestion.

In the soft capsule of the present invention, the fill material typically comprises a drug or a food.

In the soft capsule of the present invention, the content of the drug may be typically 60% or less, preferably 50% or less, more preferably 30% or less, and even more preferably 15% or less with respect to the total weight of fill material. Restricting the amount of a drug to a relatively low value makes it possible to provide a preparation wherein the unpleasant taste of the drug is especially alleviated.

Examples of a drug used in the soft capsule of the present invention include, but are not limited to, an antipyretic analgesic drug component, a rhinitis drug component, an antitussive expectorant drug component, and a vitamin component as well as a combination thereof. Examples of an antipyretic analgesic drug component include acetaminophen, aspirin, ethenzamide, salicylamide, and lactylphenetidine. Examples of a rhinitis drug component include phenylpropanolamine hydrochloride, d-chlorpheniramine maleate, dipotassium glycyrrhizinate, and belladonna leaf alkaloids. Examples of an antitussive expectorant drug component include dextromethorphan hydrobromide, codeine phosphate, methoxyphenamine hydrochloride, ephedra herb, and glycyrrhiza. Examples of a vitamin component include water-soluble vitamins, such as vitamin B and vitamin C, and fat-soluble vitamins, such as vitamin A and vitamin D. As described above, the present invention can be used preferably to provide a soft capsule for a drug having an unpleasant taste, particularly bitterness.

In the soft capsule of the present invention, the content of food may be typically 80% or less, preferably 70% or less, more preferably 50% or less, and even more preferably 30% or less with respect to the total weight of fill material.

Examples of a food used in the soft capsule of the present invention include, but are not limited to, any protein, peptide, or lipid (including steroid, carotenoid, and terpenoids), and sugars, and derivatives thereof; dried powders and extracts of any edible plant, animal, bacterium, and fungus; as well as a combination thereof.

Examples of proteins include enzymes, antibodies and collagen. Examples of enzymes include pepsine, trypsin, amylase, lipase and ribonuclease.

Examples of peptides include metabolic regulation peptides, antimicrobiral peptides, antiviral peptides and antitumor peptides.

Examples of lipids include highly unsaturated fatty acids, such as docosahexaenoic acid (DHA) and eicosapentaenoic acid (EPA).

Examples of steroids include cholesterol, sex hormones, adrenocortical hormone, sapogenin, and digitoxin.

Examples of carotenoids include lycopene, beta-carotene, and lutein.

Examples of sugars include olygosaccharides (e.g., lactose, trehalose, and maltose), polysaccharides (starch, starch hydrolysate, chondroitin sulfate, and hyaluronic acid).

Examples of edible plants include plants utilized as vegetables, fruit vegetables, or fruits (e.g., sweet pepper, carrot, tomato, water melon, melon, apple, Amorphophaleus konjac, and blueberry), and plants utilized as medical herbs (e.g., ginseng, ginkgo, *Serenoa repens*, Momordicae grosvenori, and *Garcinia cambogia*).

Examples of edible animals include mammals, birds, reptiles, arthropods, and fish. Examples of a mammal include a pig and a cow. Examples of a bird include a chicken. Examples of a reptile include a soft-shelled turtle, a turtle, and a snake. Examples of an arthropod includes a centipede and a millipede. Examples of fish include an eel.

Examples of bacteria include bifidobacterium.

Examples of fungi include yeast and mushrooms. Examples of a mushroom include a bracket fungus, a vegetative wasp, and an Agaricus.

As described above, the present invention may be utilized preferably as a soft capsule comprising a food exhibiting an unpleasant taste, such as a health food, a functional food and a nutritional supplementary food. The present invention may also be preferably utilized as a soft capsule type nonessential food having a chocolate base taste and giving a peculiar sensation of chewing.

In the soft capsule of the present invention, the shell may comprise the following components (A) and (B): (A) gelatin; and (B) a total of 100 to 600 weight parts of a plasticizer with respect to 100 weight parts of the gelatin. Such a plasticizer is typically one or more selected from (b1) to (b3) below: (b1) glycerin, (b2) a saccharide selected from the group consisting of sucrose, fructose, D-mannitol, xylitol, erythritol, D-sorbitol, maltose, reduced maltose syrup, maltitol, sucrose alcohol and isomerized sugar as well as a combination thereof (the saccharide is herein referred to as a "saccharide plasticizer"), and (b3) glycol selected from the group consisting of propylene glycol and polyethylene glycol as well as a combination thereof.

In the present invention, "gelatin" includes any of gelatin, acidic gelatin, alkaline gelatin, peptidegelatin, low molecular weight gelatin, and a derivative of gelatin (e.g., succinylated gelatin). Any of these gelatins can be used alone or in combination as the component (A) of the shell of the present invention.

One or more selected from (b1) glycerin, (b2) a saccharide plasticizer, and (b3) glycol may be used as a plasticizer of the component (B) of a shell. In the present invention, at least the glycerin (b1) is preferably used as a plasticizer component. Especially when taking into consideration easiness of molding, the glycerin (b1) is preferably used in combination with at least one of other plasticizer components, i.e., the saccharide plasticizer (b2) and the glycol (b3).

The mix amount of plasticizer in a shell is preferably a total amount of 100 to 600 weight parts of the plasticizer with respect to 100 weight parts of gelatin. When the mix amount is less than 100 weight parts, a capsule is hardened, while when the mix amount exceeds 600 weight parts, a capsule is softened but is likely to be difficult to be molded.

When the glycerin (b1) is used alone as the component (B), the amount of the glycerin (b1) used is 100 to 300 weight parts as the component (A), and particularly preferably 120 to 200 weight parts with respect to 100 weight parts of gelatin.

In the present invention, as the saccharide plasticizer (b2), one selected from sucrose, fructose, D-mannitol, xylitol, erythritol, D-sorbitol, maltose, reduced maltose syrup, maltitol, sucrose alcohol and isomerized sugar as well as a combination thereof is used. To provide sweetness when chewing, D-sorbitol, sucrose and mannitol are preferable. Considering low adhesiveness when added at a high concentration, D-sorbitol and mannitol are preferable.

When the glycerin (b1) is used in combination with the saccharide plasticizer (b2), the phase-solubility of glycerin with gelatin is excellent, and the plasticizer concentration in a shell can be increased. When glycerin is used in combination with a saccharide plasticizer, 100 weight parts of gelatin is preferably mixed with 50 to 300 weight parts of glycerin (particularly 50 to 250 weight parts), and 30 to 300 weight parts of the saccharide plasticizer (particularly, 50 to 150 weight parts).

In the present invention, as the glycol (b3), one selected from propylene glycol and polyethylene glycol is used. Polyethylene glycol having a weight average molecular weight of 400 to 4000 is particularly preferable. These glycols have a high level of hygroscopicity, and are likely to be difficult to be handled after molding, so that it is preferable that the amount of glycol to be added is not excessively large.

The combined use of the glycerin (b1) and the glycol (b3) allows a considerably soft gelatin shell. When glycerin and propylene glycol are used in combination, 100 weight parts of gelatin are preferably mixed with 40 to 200 weight parts of glycerin (particularly, 50 to 120 weight parts) and 20 to 300 weight parts of propylene glycol (particularly, 40 to 100 weight parts). When glycerin and polyethylene glycol are used in combination, 100 weight parts of gelatin is preferably mixed with 50 to 100 weight parts of glycerin (particularly, 60 to 80 weight parts) and 40 to 200 weight parts of polyethylene glycol (particularly, 50 to 100 weight parts).

When the glycerin (b1), the saccharide (b2) and the glycol (b3) are used in combination, 100 weight parts of gelatin is preferably mixed with 50 to 200 weight parts of glycerin (particularly, 60 to 150 weight parts of glycerin), 30 to 130 weight parts of saccharide (particularly, 40 to 80 weight parts of saccharide), and 20 to 120 weight parts of glycol (particularly, 50 to 100 weight parts of glycol).

In the soft capsule of the present invention, the shell can comprise water-insoluble cellulose as a component (C) in addition to gelatin as the component (A) and a plasticizer as the component (B). Examples of water-insoluble cellulose include crystalline cellulose, ethyl cellulose, low-substitution-degree hydroxypropyl cellulose and starch as well as a combination thereof. In order to prevent soft capsules from adhering to one another, crystalline cellulose is particularly preferable. The mix amount of water-insoluble cellulose is preferably 5 to 100 weight parts, and more preferably 25 to 75 weight parts with respect to 100 weight parts of gelatin. When the mix amount of water-insoluble cellulose is less than 5 weight parts with respect to 100 weight parts of gelatin, capsules are not sufficiently prevent from adhering to one another. In this case, such capsules adhere to one another or a container in preservation, or the capsules tend to cause the sensation of adhesion in the mouth. When a mix amount of water-insoluble cellulose exceeds 100 weight parts with respect to 100 weight parts of gelatin, the capsule is likely to be difficult to be molded.

In the soft capsule of the present invention, the shell further comprises any sweetening component as a component (D) (herein referred to as a "sweetener"). A sweetener may be any sweetening substance as long as it is pharmaceutically acceptable or appropriate to a food, and is compatible for production of a soft capsule. Preferable examples of a sweetener include saccharin sodium, stevia and thaumatin as well as any combination thereof.

A sweetener is optionally added to a shell, thereby making it possible to provide a preparation capable of being easily chewed in the mouth even if ingested without water.

The shell of the soft capsule of the present invention may optionally comprise a coloring agent, a preservative, a disintegrator, a surfactant, an aromatic, a flavor corrective, and a smell corrective other than the above-described components (A) through (D). Further, a weight ratio of fill material to shell is typically about 1:1 to about 4:1, preferably about 3:2 to about 3:1, and a size of a capsule is No. 3 to 20, and preferably No. 5 to 15, in view of improving the ingestion properties.

The soft capsule of the present invention may be produced by any appropriate method including a step of filling a fill material into a shell. To fill a fill material into a shell, an apparatus and procedure known in the field of production of conventional soft capsules can be utilized (see, e.g., Yamada, The Pharmaceuticals Monthly, Vol. 28, No. 4, pp. 713 to 717 (1986)).

Figure 1:
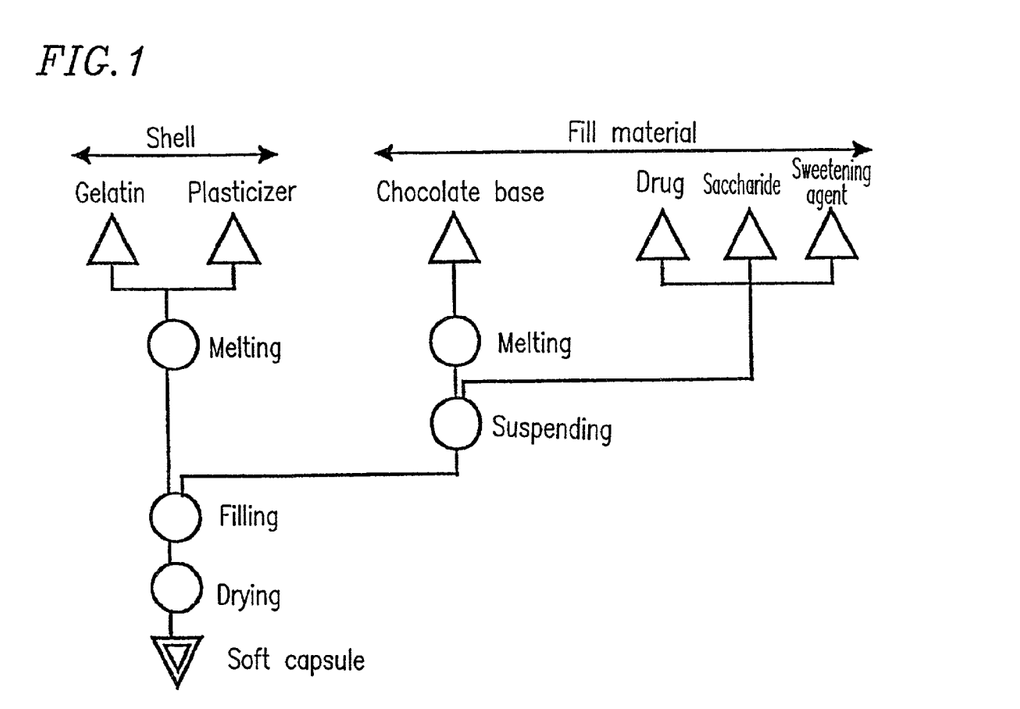
FIG. 1 is a process diagram showing an example of production of a soft capsule of the present invention.

FIG. 1 is a process diagram showing an example of production of the soft capsule of the present invention. Initially, a chocolate base (or another low melting point additive) is melted by heating. A mixture of a drug (or food), a sweetening agent and a saccharide, and optionally an aromatic are added to the melted chocolate base while heating to obtain a fill material as a uniform suspension. Separately, a shell material comprising gelatin and a plasticizer as main components is mixed, and melted by heating. The shell is filled with the fill material, whose flow property is maintained by heating, and molded, using an appropriate filling machine (e.g., an automatic rotary molding machine), optionally followed by drying in a drying chamber whose temperature is appropriately controlled. Thus, the intended soft capsule is obtained.

When the above-described drying step is continued at a desired temperature for a predetermined time or more, the fill material can experience an aging effect. As used herein, the term "aging" refers to obtaining an improvement in a physicochemical property of the fill material by keeping it at a desired temperature for a predetermined time or more. For example, when a chocolate base, particularly cacao butter, is included in the fill material, the crystal type of the cacao butter in the chocolate base can be controlled by aging.

Crystal polymorphism is present in cacao butter. When a cacao butter melt is gradually cooled, V-type and VI-type crystals which are stable forms are crystallized, thereby increasing the hardness of the cacao butter. The VI-type crystal has a hardness greater than that of the V-type crystal, but easily becomes coarse. Therefore, the VI-type crystal has been considered to be responsible for reducing ingestion properties (solubility in the mouth) (Hachiya et al., New Food Industry, 31(9), 65 to 74 (1989); and Hachiya, Yushi, 42, 50 to 58 (1989)).

The inventors have found that in production of a soft capsule comprising cacao butter as a low melting point additive, an appropriate amount of VI-type crystal such that the hardness of the cacao butter is increased to an appropriate level while ingestion properties are not reduced is crystallized by aging, so that a sense of homogeneity of the shell and the fill material is further improved. An aging temperature which allows a desired level of hardness is typically 20 to 40° C., preferably 25 to 40° C., more preferably 30 to 40° C., even more preferably 32 to 38° C., and further preferably about 35° C. The time required for aging is commonly 5 hours or more, preferably 10 hours or more, and more preferably 15 hours or more. Although there is not particularly an upper limit to the aging time, the effect of the aging time is saturated beyond a predetermined time.

Therefore, in a preferred embodiment of the present invention, cacao butter which is included in the fill material as a low melting point additive includes a major amount of V-type crystal and a minor amount of VI-type crystal. Here, "major amount" refers to an amount of crystal of a type which is present most predominantly in cacao butter crystals which is observable using X-ray diffraction. "Minor amount" refers to an amount of crystal whose present amount is relatively smaller than the major amount but is still more than or equal to a lower limit which is observable by X-ray diffraction.

Control of crystal types by aging can be applied to a case where bitter chocolate including a small amount of cacao butter is used as a low melting point additive, and further to a case where a low melting point additive other than cacao butter, which exhibits crystal morphism, is used.

The thus-obtained soft capsule of the present invention can be used preferably as a medicament, a preparation, and various foods such as a confection and a health food.

EXAMPLES

Hereinafter, specific examples of the present invention will be further disclosed. The scope of the present invention is not limited by these examples.

(Production of Soft Capsule)

All of soft capsules according to an example were produced as follows:

A chocolate base (or an alternative) was melted at about 40° C. A drug, a saccharide, a sweetening agent, and optionally an aromatic were suspended in the chocolate base while maintained at about 40° C. by heating. Thus, the fill materials were prepared. A shell was prepared by melting gelatin, a plasticizer, and optionally a sweetener at about 60° C. The shell was filled with the fill material and molded using an automatic rotary molding machine (manufactured by LEINER & SONS), followed by drying in a drying chamber at 20 to 35° C. (at a humidity of about 10 to 30%). Thus, each soft capsule was produced.

(Evaluation Method for Testing Taste)

All of taste tests were conducted for the soft capsules of the examples as follows:

Five volunteers were used as subjects. A first specimen was ingested by them without water and the taste was evaluated. Four hours after ingesting the first specimen, a second specimen was similarly ingested and evaluated. If there were third and fourth specimens, these specimens were ingested without water in the next day at an interval of four hours, and evaluated. If there was a fifth specimen, the specimen was ingested without water in the further next day, and evaluated. (Specimens listed on tables below were successively referred to as a first specimen, a second . . . from right to left.) Tastes of the specimens were evaluated in accordance with a criterion indicated in Table 1 below.

TABLE 1

| Criteria (five levels) | | |
| --- | --- | --- |
| Item | Level | Criteria |
| Unpleasant sensation of shell | 1 | present |
| Bitterness of fill material | 2 | slightly present |
|  | 3 | intermediate |
|  | 4 | almost none |
|  | 5 | none |
| Total Sensation of ingestion | 1 | bad |
|  | 2 | slightly bad |
|  | 3 | intermediate |
|  | 4 | good |
|  | 5 | considerably good |

Production Examples 1 to 5

Study of Base

Fill materials each having a formulation indicated in Table 2 were produced by the above-described method without capsulation.

TABLE 2

| Fill material formulation (mg) | | | | | | |
| --- | --- | --- | --- | --- | --- | --- |
|  | C.Ex.1 | P.Ex.1 | P.Ex.2 | P.Ex.3 | P.Ex.4 | P.Ex.5 |
| Acetaminophen | 60 | 60 | 60 | 60 | 60 | 60 |
| Bitter chocolate | — | — | — | 50 | — | 25 |

TABLE 2-continued

| | Fill material formulation (mg) | | | | | |
|---|---|---|---|---|---|---|
| | C.Ex.1 | P.Ex.1 | P.Ex.2 | P.Ex.3 | P.Ex.4 | P.Ex.5 |
| Cacao powder | — | — | — | — | 50 | 25 |
| Medium chain fatty acid triglyceride | 170 | — | 85 | — | — | — |
| Cacao butter | — | 170 | 85 | 120 | 120 | 120 |
| Xylitol | 60 | 60 | 60 | 60 | 60 | 60 |
| Total | 290 | 290 | 290 | 290 | 290 | 290 |

Results of the taste test are shown in Table 3 as averages of the judgements by the five volunteers. Comparative Example 1 as well as Production Examples 1 and 2 were separately evaluated from Production Examples 3 to 5.

TABLE 3

| | Average | | |
|---|---|---|---|
| Item of Taste test | C.EX.1 | P.Ex.1 | P.Ex.2 |
| Bitterness of fill material | 1.0 | 2.6 | 1.4 |
| Total sensation of ingestion | 1.2 | 2.8 | 1.8 |

TABLE 3-continued

| | Average | | |
|---|---|---|---|
| Item of Taste test | P.EX.3 | P.Ex.4 | P.Ex.5 |
| Bitterness of fill material | 3.2 | 3.6 | 3.4 |
| Total sensation of ingestion | 3.6 | 3.0 | 3.0 |

In Comparative Example 1 using an oil base (medium chain fatty acid triglyceride) which is a conventional formulation, the bitterness of a drug and the oiliness peculiar to the oil base were sensed immediately after ingestion, so that the sensation of ingestion was considerably bad. In Production Example 2 in which equal amounts of an oil base and cacao butter were added as apart of the fill material, the fill materials were in a semi-solid form, and the sensation of ingestion was slightly improved. In Production Example 1 in which only cacao butter as a chocolate base was added as a part of the fill materials, the fill materials were in a solid form, and bitterness and oiliness were not significantly sensed in ingesting the capsule.

Based on a formulation of Production Example 1 exhibiting a satisfactory sensation of ingestion as indicated above, bitter chocolate and/or cacao powder having a bitter taste among chocolate bases were used. In this case, the bitterness of a drug was further suppressed, and the sensation of ingestion was improved (Production Example 3 to 5). Among Production Examples 3 to 5, Production Example 3 using bitter chocolate alone was the most satisfactory.

Production Examples 6 to 13

Study of Sweetening Agents and Aromatics

Fill materials of each formulation indicated in Table 4 were produced in a manner similar to that of Production Example 1 and the like.

TABLE 4

| | Fill material formulation (mg) | | | | | | | |
|---|---|---|---|---|---|---|---|---|
| | P.Ex.6 | P.Ex.7 | P.Ex.8 | P.Ex.9 | P.Ex.10 | Ex.11 | P.Ex.12 | P.Ex.13 |
| Acetaminophen | 60 | 60 | 60 | 60 | 60 | 60 | 60 | 60 |
| Bitter chocolate | 50 | 50 | 50 | 50 | 50 | 50 | 50 | 50 |
| Cacao butter | 120 | 120 | 120 | 120 | 120 | 120 | 120 | 120 |
| Xylitol | 60 | 60 | 60 | 60 | 60 | 60 | 60 | 60 |
| Aspartame | 10 | — | — | — | — | 10 | 10 | 10 |
| Saccharin sodium | — | 3 | — | — | — | — | — | — |
| Thaumatin | — | — | 1 | — | — | — | — | — |
| Dipotassium glycyrrhizinate | — | — | — | 5 | — | — | — | — |
| Stevia | — | — | — | — | 14 | — | — | — |
| Chocolate flavor | — | — | — | — | — | 0.3 | — | — |
| Peppermint flavor | — | — | — | — | — | — | 0.3 | — |
| Vanilla flavor | — | — | — | — | — | — | — | 0.3 |
| Total | 300 | 293 | 291 | 295 | 304 | 300.3 | 300.3 | 300.3 |

Results of the taste test are shown in Table 5 as averages of the judgements by the five volunteers. Production Examples 6 to 10 were separately evaluated from Production Examples 11 to 13.

TABLE 5

| | Average | | | | |
|---|---|---|---|---|---|
| Item of taste test | P.Ex.6 | P.Ex.7 | P.Ex.8 | P.Ex.9 | P.Ex.10 |
| Bitterness of fill material | 4.0 | 3.0 | 3.4 | 3.4 | 3.4 |
| Total sensation of ingestion | 4.4 | 3.6 | 3.6 | 3.4 | 4.0 |

TABLE 5-continued

| Item of taste test | Average | | |
|---|---|---|---|
| | P.Ex.11 | P.Ex.12 | P.Ex.13 |
| Bitterness of fill material | 4.6 | 4.4 | 3.8 |
| Total sensation of ingestion | 4.8 | 4.0 | 4.2 |

Based on a formulation of Production Example 3 having a satisfactory sensation of ingestion, aspartame, saccharin sodium, thaumatin, dipotassium glycyrrhizinate or stevia were used as a sweetening agent. As a result, the bitterness of the drug was suppressed, and the sensation of ingestion was improved. Among the sweetening agents, Production Example 6 using aspartame was the most satisfactory. Based on a formulation of Production Example 6, chocolate flavor, peppermint flavor or vanilla flavor were used as an aromatic. As a result, the bitterness of the drug was further suppressed, and the sensation of ingestion was further improved. Among the aromatics, Production Example 11 using chocolate flavor was the most satisfactory.

Production Example 14 to 18

Study of Drug Content

Fill materials of each formulation indicated in Table 6 were produced in a manner similar to that of Production Example 1 and the like.

TABLE 6

| | Fill material formulation (mg) | | | | |
|---|---|---|---|---|---|
| | P.Ex.14 | P.Ex.15 | P.Ex.16 | P.Ex.17 | P.Ex.18 |
| Acetaminophen | 60 | 103 | 160 | 240 | 360 |
| Bitter chocolate | 50 | 50 | 50 | 50 | 50 |
| Cacao butter | 180 | 180 | 180 | 180 | 180 |
| Aspartame | 10 | 10 | 10 | 10 | 10 |
| Total | 300 | 343 | 400 | 480 | 600 |
| Main drug concentration (%) | 20.0 | 30.0 | 40.0 | 50.0 | 60.0 |

As described above, five volunteers were used to conduct a taste test (the result is not shown).

Acetaminophen having a relatively strong bitterness was used to study the main drug concentration which causes strong sensation of bitterness. Bitterness was somewhat suppressed until the main drug concentration is up to 50% (Production Example 17). Among these Production Examples, bitterness could be significantly suppressed when the main drug concentration was 20% (Production Example 14).

Production Examples 19 to 24

Study of Stability of Aspartame as Sweetening Agent

Fill materials of each formulation indicated in Table 7 were produced in a manner similar to that of Production Example 1 and the like.

TABLE 7

| | Fill material formulation (mg) | | | | | |
|---|---|---|---|---|---|---|
| | P.Ex.19 | P.Ex.20 | P.Ex.21 | P.Ex.22 | P.Ex.23 | P.Ex.24 |
| Acetaminophen | 60 | 60 | 60 | 60 | 60 | 60 |
| Bitter chocolate | 10 | 50 | 80 | 110 | 140 | 370 |
| Cacao butter | 160 | 120 | 90 | 60 | 30 | — |
| Xylitol | 60 | 60 | 60 | 60 | 60 | 60 |
| Aspartame (APT) | 10 | 10 | 10 | 10 | 10 | 10 |
| Total | 300 | 300 | 300 | 300 | 300 | 500 |
| Mix proportion of cacao butter (%) | 53.3 | 40.0 | 30.0 | 20.0 | 10.0 | 0.0 |
| Residual 45° C. one month rate of APT to initial value (%) | 93.1 | 96.9 | 98.2 | 98.3 | 97.6 | 91.0 |

In Production Example 20, Production Example 6 as described above was prepared again and subjected to a temporal stability test (45° C., one month). Further, the mix proportion of cacao butter was changed and studied similarly. When the mix proportion of cacao butter was 10% or more of the weight of the fill materials, the temporal stability of aspartame could be secured. Further, when the mix proportion of cacao butter was 0% in Production Example 24, a residual rate of aspartame with respect to an initial value was secured up to about 91%. Therefore, the possibility that a sufficient aspartame content is secured when the mix proportion of cacao butter is 10% or more, was demonstrated.

Production Examples 25 to 28

Differentiation Between Semi-Solid and Solid Contents

Fill materials of each formulation indicated in Table 8 were produced in a manner similar to that of Production Example 1 and the like. Forms of the fill materials were observed at a standard temperature (about 20° C.).

TABLE 8

| | Fill material formulation (mg) | | | |
|---|---|---|---|---|
| | P.Ex.25 | P.Ex.26 | P.Ex.27 | P.Ex.28 |
| Acetaminophen | 60 | 60 | 60 | 60 |
| Medium chain fatty acid triglyceride | — | 60 | 63 | 135 |
| cacao butter | 120 | 78 | 76 | 25 |
| bitter chocolate | 50 | 32 | 31 | 10 |
| xylitol | 60 | 60 | 60 | 60 |
| aspartame | 10 | 10 | 10 | 10 |
| Total | 300 | 300 | 300 | 300 |
| Proportion of low melting point additive (%) | 56.7 | 36.7 | 35.7 | 11.7 |
| Form of fill material | Solid | Solid | Semi-solid | Semi-solid |

Even if, as a base, a liquid oil base, such as medium chain fatty acid triglyceride was combined with the low melting point additives, the form of the fill materials was semi-solid when an added amount of low melting point additives, such as cacao butter and bitter chocolate, was about 10% to about 36% of the overall fill materials, and was completely solid when the amount was about 36% or more.

Examples 1 to 3

General Evaluation of Soft Capsule

Oval-type soft capsules (No. 7.5) were produced from fill materials and a shell each having a formulation indicated in Table 9. Conditions of drying after molding were a temperature of 25° C., a humidity of 20%, and a duration of 64 hours in Examples 1 to 7.

TABLE 9

| | Formulation (mg/capsule) | | | |
|---|---|---|---|---|
| | C.Ex.2 | Ex.1 | Ex.2 | Ex.3 |
| Acetaminophen | 60 | 60 | 60 | 60 |
| Medium chain fatty acid triglyceride | 170 | — | — | — |
| Cacao butter | — | 170 | 120 | 120 |
| Bitter chocolate | — | — | 50 | 50 |
| Xylitol | 60 | 60 | 60 | 60 |
| Aspartame | 10 | 10 | 10 | 10 |
| Chocolate flavor | 0.3 | 0.3 | 0.3 | 0.3 |
| Gelatin | 70 | 70 | 70 | 0 |
| Concentrated glycerin | 95 | 95 | 95 | 95 |
| Saccharin sodium | — | — | — | 2 |
| Total | 465.3 | 465.3 | 465.3 | 467.3 |

Results of taste tests are shown as averages of the judgements of the five volunteers in Table 10.

TABLE 10

| | Average | | | |
|---|---|---|---|---|
| Item of taste test | C.Ex.2 | Ex.1 | Ex.2 | Ex.3 |
| Unpleasant sensation of shell | 1.4 | 2.6 | 4.0 | 4.8 |
| Bitterness of fill material | 1.2 | 1.8 | 4.2 | 4.4 |
| Total sensation of ingestion | 1.2 | 2.2 | 4.2 | 4.6 |

In Comparative Example 2, the fill materials were in a liquid form, so that an unpleasant sensation from the shell was present, and the sensation of ingestion tended to be considerably poor. In Example 1 in which the fill materials included cacao butter and was in a solid form, although the unpleasant sensation from the shell was alleviated, a bitterness of the drug still remained slightly, and the sensation of ingestion was relatively poor. In Example 2 in which the fill materials additionally included bitter chocolate, bitterness was suppressed, and the sensation of ingestion was considerably improved. Further, it was demonstrated that when a sweetener was added to the shell (Example 3), the sensation of ingestion was further improved.

Examples 4 to 7

General Evaluation of Rhinitis Drug Formulation

Oval-type soft capsules (No. 7.5) were produced from fill materials and a shell having a formulation indicated in Table 11.

TABLE 11

| | Formulation (mg/capsule) | | | |
|---|---|---|---|---|
| | Ex.4 | Ex.5 | Ex.6 | Ex.7 |
| Phenylpropanolamine hydrochloride | 24.75 | 24.75 | 24.75 | 24.75 |
| Belladonna leaf alkaloids | 0.25 | 0.25 | 0.25 | 0.25 |
| D-chlorpheniramine maleate | 1.2 | 1.2 | 1.2 | 1.2 |
| Dipotassium glycyrrhizinate | 7.4 | 7.4 | 7.4 | 7.4 |
| Anhydrous caffeine | 20.0 | 20.0 | 20.0 | 20.0 |
| Cacao butter | 250 | 175 | 125 | 125 |
| Bitter chocolate | — | 75 | 125 | 125 |
| Xylitol | 60 | 60 | 60 | 60 |
| Aspartame | 10 | 10 | 10 | 10 |
| Chocolate flavor | 0.3 | 0.3 | 0.3 | 0.3 |
| Gelatin | 90 | 90 | 90 | 90 |
| Concentrated glycerin | 130 | 130 | 130 | 130 |
| Saccharin sodium | — | — | — | 2 |
| Total | 593.9 | 593.9 | 593.9 | 595.9 |

Results of taste tests are shown as averages of the judgements of the five volunteers in Table 12.

TABLE 12

| | Average | | | |
|---|---|---|---|---|
| Item of taste test | Ex.4 | Ex.5 | Ex.6 | Ex.7 |
| Unpleasant sensation of shell | 2.6 | 3.2 | 4.2 | 4.8 |
| Bitterness of fill material | 1.6 | 2.8 | 4.4 | 4.6 |
| Total sensation of ingestion | 2.0 | 3.4 | 4.4 | 4.8 |

In Example 4, the main fill material was cacao butter, so that the unpleasant sensation from the shell was not considerably sensed, but bitterness of a drug slightly remained, and the sensation of ingestion was relatively poor. In Examples 5 and 6 in which bitter chocolate was further included in the fill material, bitterness was suppressed, and the sensation of ingestion was considerably improved. Among the examples, in Example 6 in which the amount of bitter chocolate added was increased, bitterness was further suppressed, and the sensation of ingestion is improved. In Example 7 in which a sweetener was added to the shell, it was demonstrated that the sensation of ingestion was further improved similarly to Example 3 above.

(Criterion of Usability)

Usability of soft capsules was evaluated in the following examples in accordance with a criterion indicated in Table 13 below.

TABLE 13

| Criterion for usability | | |
|---|---|---|
| Item of test | Level | Criterion |
| Usability | 1 | Bad |
| Ease of removing capsule | 2 | Slightly bad |
| from PTP package by pressing | 3 | Intermediate |
| | 4 | Good |
| | 5 | Considerably good |

Examples 8 to 11

General Evaluation of Formulation Including Water-Insoluble Cellulose (a) Antipyretic Analgesic Drug Formulation Oval-type soft capsules (No. 7.5) were produced from fill materials and a shell each having a formulation indicated in Table 14.

TABLE 14

| Formulation (mg/capsule) | | | |
|---|---|---|---|
| | Ex.8 | Ex.9 | C.Ex.3 |
| Acetaminophen | 53.6 | 53.6 | 53.6 |
| Medium chain fatty acid triglyceride | — | — | 250 |
| Cacao butter | 150.0 | 175.0 | — |
| Bitter chocolate | 100.0 | — | — |
| Cacao powder | — | 75.0 | — |
| Xylitol | 80.0 | 80.0 | 80.0 |
| Aspartame (APT) | 15.0 | 15.0 | 15.0 |
| Chocolate flavor | 0.4 | 0.4 | 0.4 |
| Succinylated gelatin | 70 | 70 | 70 |
| Concentrated glycerin | 90 | 90 | 90 |
| Crystalline cellulose | 25 | 25 | 25 |
| Titanium oxide | 0.34 | 0.34 | 0.34 |
| Red No. 102 | 0.55 | 0.55 | 0.55 |
| Yellow No. 5 | 0.14 | 0.14 | 0.14 |
| Blue No. 1 | 0.02 | 0.02 | 0.02 |
| Total | 585.05 | 585.05 | 585.05 |

Results of taste tests and usability tests are shown as averages of the judgements of the five volunteers in Table 15.

TABLE 15

| | Average | | |
|---|---|---|---|
| Item of taste test and usability test | Ex.8 | Ex.9 | C.Ex.3 |
| Unpleasant sensation of shell | 4.8 | 4.8 | 1.4 |
| Bitterness of fill material | 4.4 | 4.6 | 1.6 |
| Total sensation of ingestion | 4.6 | 4.6 | 1.2 |
| Usability | 4.6 | 4.6 | 1.2 |

In Comparative Example 3, since the fill materials were in a liquid form, an unpleasant sensation from the shell was present, and the sensation of ingestion tended to be poor. The soft capsule of Comparative Example 3 tended to be significantly difficult to remove from a PTP (Press Through Pack) package by pressing.

In Examples 8 and 9, cacao butter was used as a base, and bitter chocolate or cacao powder was added to the fill materials, so that the fill materials were in a solid form. In the examples, the unpleasant sensation from the shell was alleviated, bitterness was further suppressed, and the sensation of ingestion was considerably improved. In Examples 8 and 9, a shell of soft capsules included crystalline cellulose which is a kind of water-insoluble cellulose. For the soft capsules of examples 8 and 9, an unpleasant sensation from the capsules was substantially not present. In observation in a sealed glass bin at 40° C. for one month storage, the capsules substantially did not adhere to one another. Further, the solid form of the fill materials allowed the soft capsule to be easily removed from a PTP package by pressing. Therefore, it was demonstrated that the formulations of Examples 8 and 9 are excellent products from a viewpoint of practical utility.

(b) Rhinitis Drug Formulation

Oval-type soft capsules (No. 7.5) were produced from fill materials and a shell having a formulation indicated in Table 16.

TABLE 16

| Formulation (mg/capsule) | | |
|---|---|---|
| | Ex.10 | Ex.11 |
| Phenylpropanolamine hydrochloride | 24.75 | 24.75 |
| Belladonna leaf alkaloids | 0.25 | 0.25 |
| Dipotassium glycyrrhizinate | 7.4 | 7.4 |
| Anhydrous caffeine | 20.0 | 20.0 |
| D-chlorpheniramine maleate | 1.2 | 1.2 |
| Cacao butter | 150.0 | 175.0 |
| Bitter chocolate | 100.0 | — |
| Cacao powder | — | 75.0 |
| Xylitol | 80.0 | 80.0 |
| Aspartame (APT) | 15.0 | 15.0 |
| chocolate flavor | 0.4 | 0.4 |
| Succinylated gelatin | 70 | 70 |
| Concentrated glycerin | 90 | 90 |
| Crystalline cellulose | 25 | 25 |
| Titanium oxide | 0.34 | 0.34 |
| Red No. 102 | 0.55 | 0.55 |
| Yellow No. 5 | 0.14 | 0.14 |
| Blue No. 1 | 0.02 | 0.02 |
| Total | 585.05 | 585.05 |

Results of taste tests and usability tests are shown as averages of the judgements of the five volunteers in Table 17.

TABLE 17

| | Average | |
|---|---|---|
| Item of taste test and usability test | Ex.8 | Ex.9 |
| Unpleasant sensation of shell | 4.8 | 4.8 |
| Bitterness of fill material | 4.4 | 4.6 |
| Total sensation of ingestion | 4.6 | 4.6 |
| Usability | 4.6 | 4.6 |

In rhinitis drug formulations of Examples 10 and 11, similarly to Examples 8 and 9 above, the unpleasant sensation from the shell was alleviated, bitterness was suppressed, and the total sensation of ingestion was significantly satisfactory. Usability was also evaluated highly. Therefore, it was demonstrated that the formulations of Examples 10 and 11 are excellent products from a viewpoint of practical utility.

Production Example 29 and 30

Study of Aging (a) Study of Aging Temperature

The same formulation fill materials as those in Example 8 (Production Example 29) were prepared and melted in a manner similar to that of Production Example 1 above or the like. Thereafter, the resultant fill materials were subjected to aging in a drying chamber at 25° C., 30° C., 35° C., 37° C., and 40° C. for 16 hours. As a control, cacao butter alone was solely subjected to the same procedure. After aging, the fill materials were cooled and solidified in the shape of a capsule. Hardness of the solidified fill materials and cacao butter in a minor axis direction of breadth was measured using a manual tablet hardness tester (manufactured by Pfizer Inc.).

Figure 2:
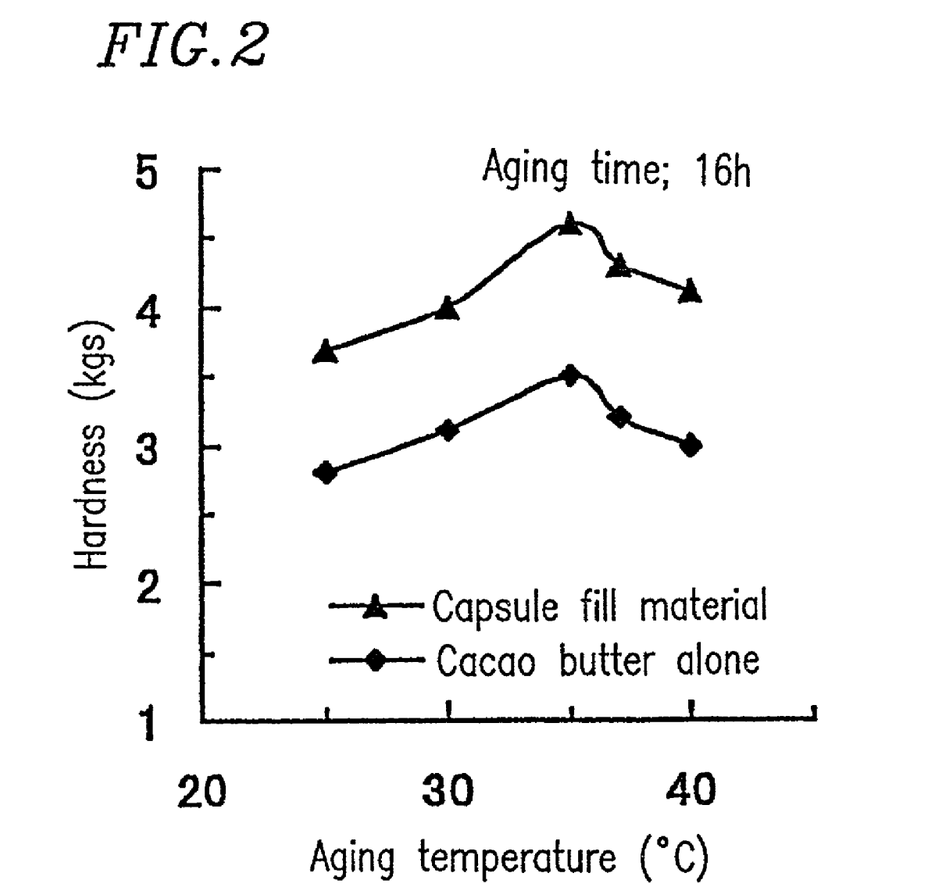
FIG. 2 is a graph showing the change in hardness of capsule fill material and cacao butter with respect to aging temperature. The vertical axis represents hardness (kgs), while the horizontal axis represents aging temperature (° C.). Black triangles represent results for the capsule fill material. Black diamonds represent results for cacao butter alone.

Results are shown in FIG. 2. The hardness of the capsule fill materials and cacao butter were both gradually increased with an increase in aging temperature. The hardness reached a peak at 35° C. and tended to fall at higher temperatures. The change in hardness of the capsule fill materials and the change in hardness of cacao butter alone had the same temperature dependent pattern. Therefore, it was demonstrated that a physical property of cacao butter is a dominant cause for an increase in hardness of the capsule fill materials. In this case, cacao butter subjected to aging at 35° C. included mainly V-type crystal and subordinately VI-type crystal according to X-ray diffraction analysis.

(b) Study of Aging Time

The same fill materials as those in Example 8 (Production Example 30) were prepared and melted in a manner similar to that of Production Example 1 above or the like. Thereafter, the resultant fill materials were subjected to aging in a drying chamber at 35° C. for 0, 2, 6, 8, 12, 16 and 64 hours. As a control, cacao butter alone was solely subjected to the same procedure. After aging, the fill materials and cacao butter were cooled and made solid in the shape of a capsule. The hardness of solidified fill materials and cacao butter was measured in a manner similar to that of above section (a).

Figure 3:
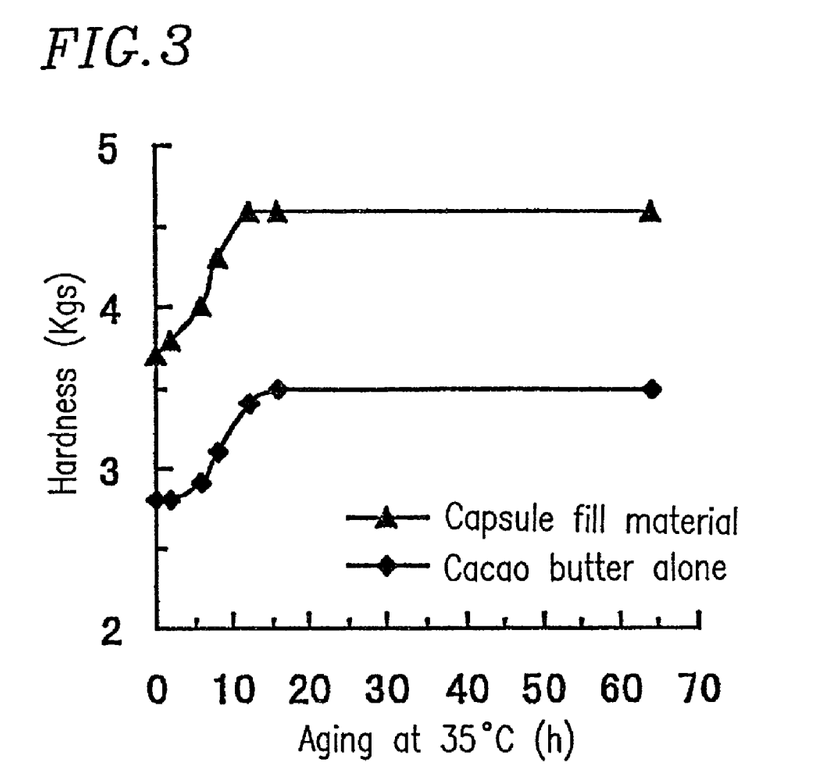
FIG. 3 is a graph showing the change in hardness of capsule fill material and cacao butter with respect to aging time. The vertical axis represents hardness (kgs), while the horizontal axis represents aging time at 35° C. Black triangles represent results for the capsule fill material. Black diamonds represent results for cacao butter alone.

Results are shown in FIG. 3. The hardness of the capsule fill materials and cacao butter were both gradually increased with an increase in aging time until 16 hours. After 16 hours and 64 hours, no further difference was found. Therefore, it was demonstrated that a near-maximal hardness is obtained by aging at 35° C. for 16 hours or more.

Example 12

General Evaluation of Aged Soft Capsule

Soft capsules were produced using the same fill materials and shell as those in Example 8. After molding, a first group of the soft capsules were subjected to aging at 35° C. for 16 hours (Example 12), and a second group of the soft capsules were not subjected to aging but were cooled at 25° C. (Example 13). Each of the resultant soft capsules were subjected to a taste test and a usability test.

Figure 4:
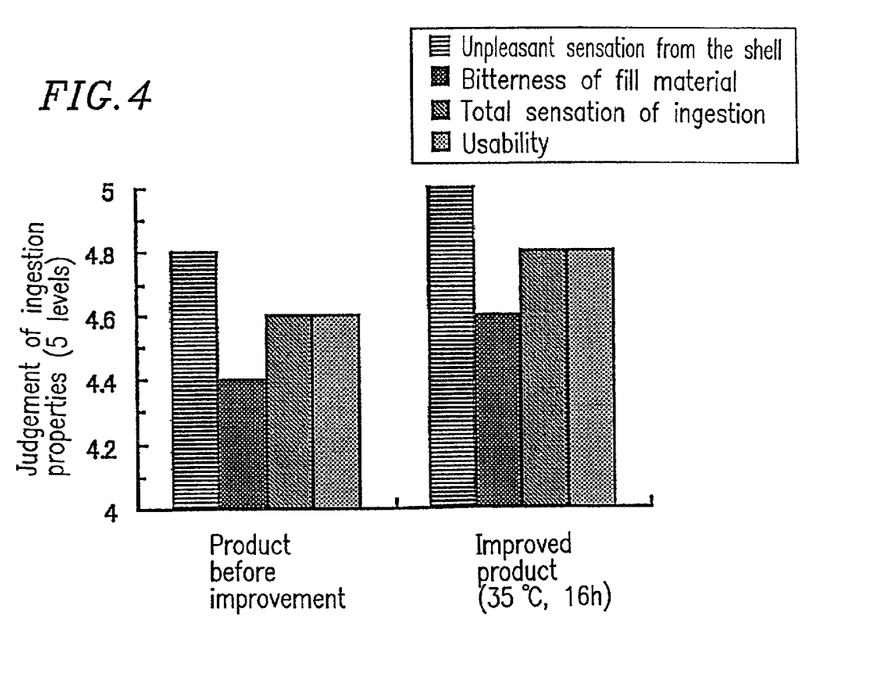
FIG. 4 is a graph showing the results of a taste test and a usability test for soft capsules produced with or without aging. The vertical axis represents mean values for each item judged by five volunteers in a five-level evaluation. The four left-hand columns (products before improvement) show results without aging, while right four columns (improved products) show results with aging. The columns represent, from left, the unpleasant sensation from the shell, the bitterness of the fill material, the total sensation of ingestion, and usability.

Results are shown in FIG. 4. As compared to the non-aged soft capsules, the aged soft capsules had a further alleviated unpleasant sensation from the shell, further suppressed bitterness of the drug, and improved evaluation of the total sensation of ingestion and usability. Therefore, it was demonstrated that when the fill materials of a formulation include cacao butter, aging allows an especially satisfactory soft capsule.

INDUSTRIAL APPLICABILITY

According to the present invention, the fill materials of a soft capsule are formulated in such a manner as to be in a solid or semi-solid form at room temperature. Therefore, when chewing the soft capsule, the shell and the fill materials are homogenized, thereby making it possible to alleviate the unpleasant sensation from the shell. Particularly, when a low melting point additive, such as a chocolate base, are formulated as a fill material of the soft capsule, a preparation capable of being easily chewed in the mouth without water is obtained. Such a chewable soft capsule is useful as an immediate-soluble drug and food, especially for children or elderly users.

When fill materials are in a solid form, a soft capsule containing a fill material can be easily removed from a packaging container, resulting in satisfactory usability. When a shell includes water-insoluble cellulose, the effect that capsules are unlikely to adhere to one another in preservation is obtained. Thus, the present invention can provide a soft capsule having practical utility as a product.

When a soft capsule is subjected to aging after a shell is filled with fill materials, the sensation of ingestion and usability can be particularly improved in a case where a chocolate base, particularly cacao butter, is used as a low melting point additive.

The invention claimed is:

1. A method for producing a soft capsule comprising:
   melting a low melting point additive comprising a chocolate base comprising cacao butter to produce a fill material, wherein the fill material has a hardness of no greater than 47 kgs;
   producing a shell;
   filling the shell with the fill material; and
   drying the filled material in a drying chamber at a temperature of 30° C. to 40° C. for 5 hours to 64 hours so that a major amount of V-type cacao butter crystals and a minor amount of VI-type cacao butter crystals are formed such that the shell and fill material are homogenized with each other to produce the soft capsule.

2. A method for producing a soft capsule according to claim 1, wherein the content of the low melting point additive is 10% or more with respect to the total weight of the fill material.

3. A method for producing a soft capsule according to claim 2, wherein the content of the low melting point additive is 30% or more with respect to the total weight of the fill material.

4. A method for producing a soft capsule according to claim 3, wherein the content of the low melting point additive is 50% or more with respect to the total weight of the fill material.

5. A method for producing a soft capsule according to any one of claims 1, 2, 3, or 4, wherein the melting point of the low melting point additive is about 20 to 50° C.

6. A method for producing a soft capsule according to any one of claims 1, 2, 3, or 4, wherein the low melting point additive further comprises a second ingredient selected from lard, coconut oil, polyethylene glycol, or combinations thereof.

7. A method for producing a soft capsule according to claim 1, wherein the chocolate base further comprises bitter chocolate.

8. A method for producing a soft capsule according to claim 1, wherein the fill material further comprises a sweetening agent.

9. A method for producing a soft capsule according to claim 8, wherein the sweetening agent is selected from the group consisting of aspartame, disodium glycyrrhizinate, saccharin sodium, stevia and thaumatin as well as a combination thereof.

10. A method for producing a soft capsule according to claim 9, wherein the fill material comprises cacao butter and aspartame.

11. A method for producing a soft capsule according to claim 8, wherein the fill material further comprises a saccharide.

12. A method for producing a soft capsule according to claim 11, wherein the saccharide is selected from the group consisting of sucrose, D-mannitol, xylitol, erythritol, D-sorbitol, maltose, reduced maltose syrup and maltitol as well as a combination thereof.

13. A method for producing a soft capsule according to claim 8, wherein the fill material further comprises an aromatic.

14. A method for producing a soft capsule according to claim 13, wherein the aromatic is chocolate flavor.

15. A method for producing a soft capsule according to claim 1, wherein the shell comprises the following components (A) and (B):
(A) gelatin; and
(B) one or more plasiticizers selected from (b1) to (b3), wherein a total of 100 to 600 weight parts of the plasticizers is present in the shell with respect to 100 weight parts of gelatin:
(b1) glycerin,
(b2) saccharide plasticizer selected from the group consisting of sucrose, fructose, D-mannitol, xylitol, erythritol, D-sorbitol, maltose, reduced maltose syrup, maltitol, sucrose alcohol and isomerized sugar as well as a combination thereof, and
(b3) glycol selected from the group consisting of propylene glycol and polyethylene glycol as well as a combination thereof.

16. A method for producing a soft capsule according to claim 15, wherein the plasticizers (B) include the glycerin (b1).

17. A method for producing a soft capsule according to claim 15, wherein the shell further comprises (C) water-insoluble cellulose, wherein 5 to 100 weight parts of water-insoluble cellulose is present in the shell with respect to 100 weight parts of the gelatin.

18. A method for producing a soft capsule according to claim 15, wherein the shell further comprises (D) a sweetener.

19. A method for producing a soft capsule according to claim 18, wherein the sweetener (D) is selected from the group consisting of saccharin sodium, stevia and thaumatin as well as a combination thereof.

20. A method for producing a soft capsule according to claim 1, wherein the fill material further comprises a drug.

21. A method for producing a soft capsule according to claim 20, wherein the content of the drug is 60% or less with respect to the total weight of the fill material.

22. A method for producing a soft capsule according to claim 21, wherein the drug is selected from the group consisting of an antipyretic analgesic drug component, a rhinitis drug component, an antitussive expectorant drug component and a vitamin component as well as a combination thereof.

23. A method for producing a soft capsule according to claim 1, wherein the fill material further comprises a food.

24. A method according to claim 1, wherein the drying is conducted for 10 hours to 64 hours.

25. A method for producing a soft capsule according to claim 6, wherein the second ingredient is lard.

26. A method for producing a soft capsule according to claim 6, wherein the second ingredient is coconut oil.

27. A method for producing a soft capsule according to claim 6, wherein the second ingredient is polyethylene glycol.

28. A method for producing a soft capsule according to any one of claims 1, 2, 3, or 4, wherein the melting point of the low melting point additive is about 20 to 50° C. and wherein the low melting point additive further comprises lard, coconut oil, polyethylene glycol, or combinations thereof.

29. A method for producing a soft capsule of claim 1, wherein the drying is conducted for 5 hours to 16 hours at a temperature of about 35° C.

* * * * *